US008699657B2

(12) United States Patent  
Baeumer et al.

(10) Patent No.: US 8,699,657 B2  
(45) Date of Patent: Apr. 15, 2014

(54) X-RAY EXAMINATION APPARATUS AND METHOD

(75) Inventors: Christian Baeumer, Dorsten-rhade (DE); Gereon Vogtmeier, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 395 days.

(21) Appl. No.: 13/139,308

(22) PCT Filed: Dec. 10, 2009

(86) PCT No.: PCT/IB2009/055661  
§ 371 (c)(1),  
(2), (4) Date: Jul. 25, 2011

(87) PCT Pub. No.: WO2010/070554  
PCT Pub. Date: Jun. 24, 2010

(65) Prior Publication Data  
US 2011/0280367 A1 Nov. 17, 2011

(30) Foreign Application Priority Data  
Dec. 17, 2008 (EP) .................................... 08171891

(51) Int. Cl.  
*H05G 1/70* (2006.01)  
*H05G 1/56* (2006.01)  
*H05G 1/32* (2006.01)  
*H05G 1/10* (2006.01)  
*H05G 1/02* (2006.01)  
*H01J 35/06* (2006.01)

(52) U.S. Cl.  
USPC ................ 378/9; 378/92; 378/98.9; 378/112; 378/114; 378/134; 250/494.1

(58) Field of Classification Search  
USPC ........ 378/4–20, 91, 92, 98, 98.8, 98.9, 98.11, 378/98.12, 101, 111, 112, 114, 115, 119, 378/121–124, 134, 204, 901; 250/370.01, 250/370.08, 370.09, 371, 393–395, 370.06, 250/494.1, 526  
See application file for complete search history.

(56) References Cited

U.S. PATENT DOCUMENTS 6,876,724 B2 4/2005 Zhou et al.  
(Continued)

FOREIGN PATENT DOCUMENTS

JP 2006320464 A 11/2006  
(Continued)

OTHER PUBLICATIONS

Deman, B., et al.; Inverse geometry CT: The next-generation CT architecture; 2007; IEEE Nuclear Science Symposium Conf. Record; 2715-2716.

(Continued)

*Primary Examiner* — Anastasia Midkiff (57) ABSTRACT

The present invention relates to an examination apparatus and a corresponding method to realize a Spectral x-ray imaging device through inverse-geometry CT. The proposed examination apparatus comprises: an X-ray source unit (14) comprising a plurality of X-ray sources (15) for emitting X-rays (24) at a plurality of locations, an X-ray detection unit (18) for detecting X-rays emitted from one or more of said X-ray sources (15) after penetration of an examination area (19) between said X-ray source unit (14) said X-ray detection unit (18) and for generating detection signals, a processing unit (36) for processing the generated detection signals, and—a control unit (26) for controlling said X-ray sources (15) to subsequently, alone or in groups emit X-rays at least two different energy spectra such that in the time interval, during which a particular X-ray source (15a) or said group of X-ray sources (15a,15d, 15g), is switched over to emit X-rays at a different energy spectrum, said particular X-ray source (15a) or said group of X-ray sources (15a, 15d, 15g) is switched off and one or more other X-ray sources (15b, 15c) or groups of X-ray sources (15b, 15e, 15h; 15c, 15f, 15i) are subsequently switched on to emit X-rays.

20 Claims, 6 Drawing Sheets

(56) References Cited

U.S. PATENT DOCUMENTS

| | | |
|---|---|---|
| 7,103,137 B2 * | 9/2006 | Seppi et al. .................. 378/9 |
| 7,110,500 B2 | 9/2006 | Leek |
| 7,876,874 B2 | 1/2011 | Goto et al. |
| 7,968,853 B2 | 6/2011 | Altman et al. |
| 2005/0226364 A1 | 10/2005 | Bernard De Man et al. |
| 2006/0210015 A1 | 9/2006 | Pelc et al. |
| 2008/0049891 A1 | 2/2008 | Yin et al. |
| 2008/0192890 A1 | 8/2008 | Nisius |
| 2009/0003514 A1 * | 1/2009 | Edic et al. .................. 378/10 |
| 2009/0220043 A1 * | 9/2009 | Nishide et al. .............. 378/19 |
| 2010/0183117 A1 * | 7/2010 | Tsumuraya et al. ........... 378/9 |

FOREIGN PATENT DOCUMENTS

| | | |
|---|---|---|
| JP | 2007267980 A | 10/2007 |
| WO | 2007038306 A2 | 4/2007 |
| WO | 2007088497 A1 | 8/2007 |
| WO | 2007140093 A1 | 12/2007 |

OTHER PUBLICATIONS

Dobbins III, J. T., et al.; Digital x-ray tomosynthesis: current state of the art and clinical potential; 2003; Phys. Med. Biol.; 48:R65-R106.

Iwanczyk, J. S., et al.; Photon Counting Energy Dispersive Detector Arrays for X-ray Imaging; 2007; IEEE Nuclear Science Symposium Conf. Record; 2741-2748.

Mazin, S. R., et al.; Adaptation of a Fast 3D PET Reconstruction Algorithm to an Inverse-Geometry CT System; 2006; IEEE Nuclear Science Symposium Conf. Record; vol. 4; abstract.

Schmidt, T. G., et al.; An inverse-geometry volumetric CT system with a large-area scanned source: A feasibility study; 2004; Med. Phys.; 31(9)2623-2627.

Liu, Z., et al.; Carbon nanotube based microfocus field emission x-ray source for microcomputed tomography; 2006; Applied Physics Letters; 89:103111-1-03111-3.

Wang, G., et al.; An outlook on x-ray CT research and development; 2008; Med. Phys.; 35(3)1051-1064.

* cited by examiner

X-RAY EXAMINATION APPARATUS AND METHOD

FIELD OF THE INVENTION

The present invention relates to an X-ray examination apparatus and a corresponding method as well as a computer program for control of said apparatus.

BACKGROUND OF THE INVENTION

Color (or spectral) X-ray imaging has been identified as most promising route for future development of CT (Computer Tomography) by all vendors of medical CT scanners. However, CT vendors obviously follow different approaches to enter the spectral domain. This is mainly given due to the fact that hardware realization of a spectral CT scanner is a non-trivial task.

In a novel 'inverse' geometry CT (IGCT) system design, as described, for instance, in DeMan, B. et al., "Inverse geometry CT: The next-generation CT architecture?", IEEE Nuclear Science Symposium Conference Record, 2007, M07-2, p. 2715-2716, a large distributed X-ray source with an array of discrete electron emitters and focal spots, and a high frame-rate flat-panel X-ray detector is used. With the advent of carbon-nanotubes (CNTs), as described, for instance, in Liu, Z. et al., "Carbon nanotube based microfocus field emission x-ray source for microcomputed tomography", Applied Physics Letters 89, 103111 (2006), as cold 'electron-guns' fast switchable X-ray generators can be built. Such CNT-based X-ray sources can be arranged in an array-like manner in such an inverse CT system, where they are switched on and off in time according to a predetermined modulation pattern.

Known spectral CT systems have to overcome the following technical hurdles or have the following drawbacks:

Dual-source CT systems with dissimilar kVp (peak kilovoltage) settings: only two material components can be unambiguously separated; high hardware costs, since two sources and two detectors have to be mounted.

Dual-layer detector: only two material components can be unambiguously separated; complex production process of the detector.

Fast dual kVp switching: only two material components can be unambiguously separated; low spectral separation, since strong kV transients are difficult to realize.

Photon-counting spectral CT: detection requires high hardware effort.

SUMMARY OF THE INVENTION

It is an object of the present invention to provide an X-ray examination apparatus, in particular having an inverse CT geometry, and a corresponding method as well as a computer program for control of said apparatus by which the above mentioned hurdles and drawbacks can be overcome.

In a first aspect of the present invention an X-ray examination apparatus is presented comprising:
- an X-ray source unit comprising a plurality of X-ray sources for emitting X-rays at a plurality of locations,
- an X-ray detection unit for detecting X-rays emitted from one or more of said X-ray sources after penetration of an examination area between said X-ray source unit and said X-ray detection unit and for generating detection signals,
- a processing unit for processing the generated detection signals, and
- a control unit for controlling said X-ray sources to subsequently, alone or in groups emit X-rays at least two different energy spectra such that in the time interval, during which a particular X-ray source or said group of X-ray sources is switched over to emit X-rays at a different energy spectrum, said particular X-ray source or said group of X-ray sources is switched off and one or more other X-ray sources or groups of X-ray sources are subsequently, alone or in groups switched on to emit X-rays.

In a further aspect of the present invention a corresponding method is presented.

In still a further aspect of the present invention a computer program is presented comprising program code means for causing a computer to control the X-ray examination apparatus as defined above to carry out the steps of the method as claimed mentioned above when said computer program is carried out on a computer.

Preferred embodiments of the invention are defined in the dependent claims. It shall be understood that the claimed method and the claimed computer program has similar and/or identical preferred embodiments as the claimed device and as defined in the dependent claims.

The present invention is based on the idea to use an inverse CT system arrangement in which preferably only one X-ray source or a group of (but not all) X-ray sources is active at a given time, particularly for spectral CT applications. To switch a particular X-ray source, or said group of X-ray sources, over to achieve that it emits X-rays at a different energy spectrum than before, as is required for spectral CT applications, takes some time. This time of switching over a particular X-ray source, or said group of X-ray sources, is exploited according to the present invention to switch this particular X-ray source, or said group of X-ray sources, off (so that it does not emit any X-ray radiation) and to switch on one or more X-ray sources or groups of X-ray source—subsequently and preferably only one or one group at a time—to emit X-ray radiation in the meantime. Thus, during this time detection signals are also obtained which saves much time. Hence, according to the present invention the inverse-CT source modulation pattern is extended by an advantageous alternating kV modulation scheme.

Further advantages are a reduced acquisition time which, in turn, leads to less motion artifacts, as well as a better temporal resolution. If non-ideal effects are regarded, the switching can be described by a transient behavior. For example, considering a "slow" thermal emitter at the source or "afterglow" in the detector, then there is less overlap of different energy spectra, if the signal from the previous frame leaks into the current acquisition frame.

According to an embodiment said control unit is adapted for controlling said X-ray sources such that the particular X-ray source or said group of X-ray sources is switched over to emit X-rays at said different energy spectrum as fast as possible. Hence, only during a minimum time duration other X-ray sources are switched on. As soon as the process of switching over the first (particular) X-ray source or said first group of X-ray sources is finished, this X-ray source (or group of X-ray sources) is switched on again to emit X-rays at the new energy spectrum. Preferably, this time duration is determined in advance to control the timing of the switching of the X-ray sources appropriately. However, it is also possible to determine the time duration and the timing 'online' during the switching process itself.

According to another embodiment said control unit is adapted for controlling said X-ray sources such that said one or more other X-ray sources or groups of X-ray sources, which are subsequently switched on to emit X-rays during said time interval during which said particular X-ray source or said group of X-ray sources is switched over, are emitting X-rays at the energy spectrum, at which said particular X-ray source or said group of X-ray sources had previously emitted X-rays or will emit X-rays after it has been switched over. Thus, all the detection signals during a certain time period (and from a certain range of projection angles) are acquired at the same energy spectrum of X-ray radiation which might be advantageous during data processing and reconstruction. Parts of the acquisition can also be done with one fixed spectrum while other parts could be acquired in dual or multi energy mode depending on the region of interest, which leads to more flexibility.

It is further preferred that said control unit is adapted for controlling said X-ray sources to emit X-rays in groups such that X-ray sources of a first group of X-ray sources are alone, separately and subsequently emitting X-rays at the at least two different energy spectra and that thereafter X-ray sources of other groups of X-ray sources are alone, separately and subsequently emitting X-rays at the at least two different energy spectra. The advantage is a different group size as optimization with respect to minimization of the number of spectrum switching activities, but also a high enough temporal resolution There are various options available to switch over the X-ray source to emit X-ray radiation at a different energy spectrum. Preferably, said control unit is adapted for switching over said X-ray sources to emit X-rays at a different energy spectrum by changing the X-ray source voltage, in particular the voltage provided to the anode of an X-ray source. This allows a simple control of the X-ray sources and the switching process.

For this purpose, the apparatus preferably further comprises a high voltage supply unit having a number of high voltage supply lines, wherein said control unit comprises a multiplexer for dynamically connecting said X-ray sources to the respective supply lines according to a switching pattern.

According to an advantageous embodiment said X-ray sources are distributed X-ray sources, in particular field emitter based X-ray sources, such as (e.g. microfocus) X-ray sources with carbon nanotube based field emitter. Such distributed X-ray sources are space saving and can be easily controlled. Further, the acquisition can be much faster if CNTs are used, which can be arranged as array on a planar substrate. Further, also a conventional thermal emitter technology could be used to build distributed X-ray sources. Still further, scatter artefacts are minimized. Furthermore, distributed X-ray sources allow to examine the object from different viewing angles without mechanical movement. The set of projection images from different viewing angles allow for a limited 3D image reconstruction (e.g. tomosynthesis). This tomographic imaging scheme simplifies construction and operation of the imaging device.

Preferably, the apparatus further comprises a gantry on which said X-ray source unit and said X-ray detection unit are mounted and which is configured to rotate around said examination area. In particular, the gantry could be arranged such that one or more or each of said unit can rotate around said examination area. The advantage of using distributed X-ray sources is that such an apparatus does not require mechanical movement/rotation. In other embodiments, a gantry is provided, in particular for movement/rotation of the X-ray sources and/or the detector. On such a gantry, also a distributed X-ray source unit can be used.

In a preferred embodiment said X-ray detection unit comprises a multi-layer detector, in particular a dual-layer detector, each layer being adapted for detecting X-rays at a predetermined energy spectrum. Thus, hardware costs are reduced, because detectors in inverse geometry cover a smaller X-ray sensitive area. Such a dual-layer detector per se is, for instance, described in WO 2007/039840 A2.

According to another embodiment said X-ray detection unit comprises a energy discriminating, photon counting detector. Also with this embodiment a reduction of hardware costs due to less detector area is achieved compared to conventional CT detector size. Such a energy-discrimination photon-counting detector is, for instance, described in Iwanczyk, J., S. et al., "Photon Counting Energy Dispersive Detector Arrays for X-ray Imaging", IEEE Nuclear Science Symposium Conference Record, 2007, M09-4, p. 2741-2748.

Still further, according to an embodiment the apparatus comprises overflow detection means for detecting if during an X-ray detection there is an overflow in any pixel of the X-ray detector, and said control unit is adapted to reduce the current provided to the active X-ray source.

It is also possible that the control unit is adapted for, e.g. adaptively, determining an optimized switching scheme taking into account the hardware, in particular the high-voltage generator, the switching times (of the sources, e.g. the CNTs), the region of interest, and the required spatial resolution.

In an embodiment said control unit is adapted for controlling said X-ray sources to emit X-rays in groups such that a first group of X-ray sources are emitting X-rays with overlapping energy spectra and that thereafter other groups of X-ray sources are separately and subsequently emitting X-rays at, in particular the same, energy spectrum. This embodiment provides the advantage that with an energy-resolving detector the source can be identified leading to a fast acquisition time and high accuracy.

BRIEF DESCRIPTION OF THE DRAWINGS

These and other aspects of the invention will be apparent from and elucidated with reference to the embodiment(s) described hereinafter. In the following drawings

Like reference numbers refer in the Figures to identical or similar components.

DETAILED DESCRIPTION OF THE INVENTION

The present technique is generally directed towards an imaging technique, such as a tomosynthesis imaging technique, to generate useful images for medical and non-medical applications. As will be appreciated by those of ordinary skill in the art, the present techniques may be applied in various medical and non-medical applications, such as passenger and/or baggage screening, to provide useful three-dimensional data and context. To facilitate explanation of the present techniques, however, a medical implementation will be generally discussed herein, though it is to be understood that non-medical implementations are also within the scope of the present techniques.

Figure 1:
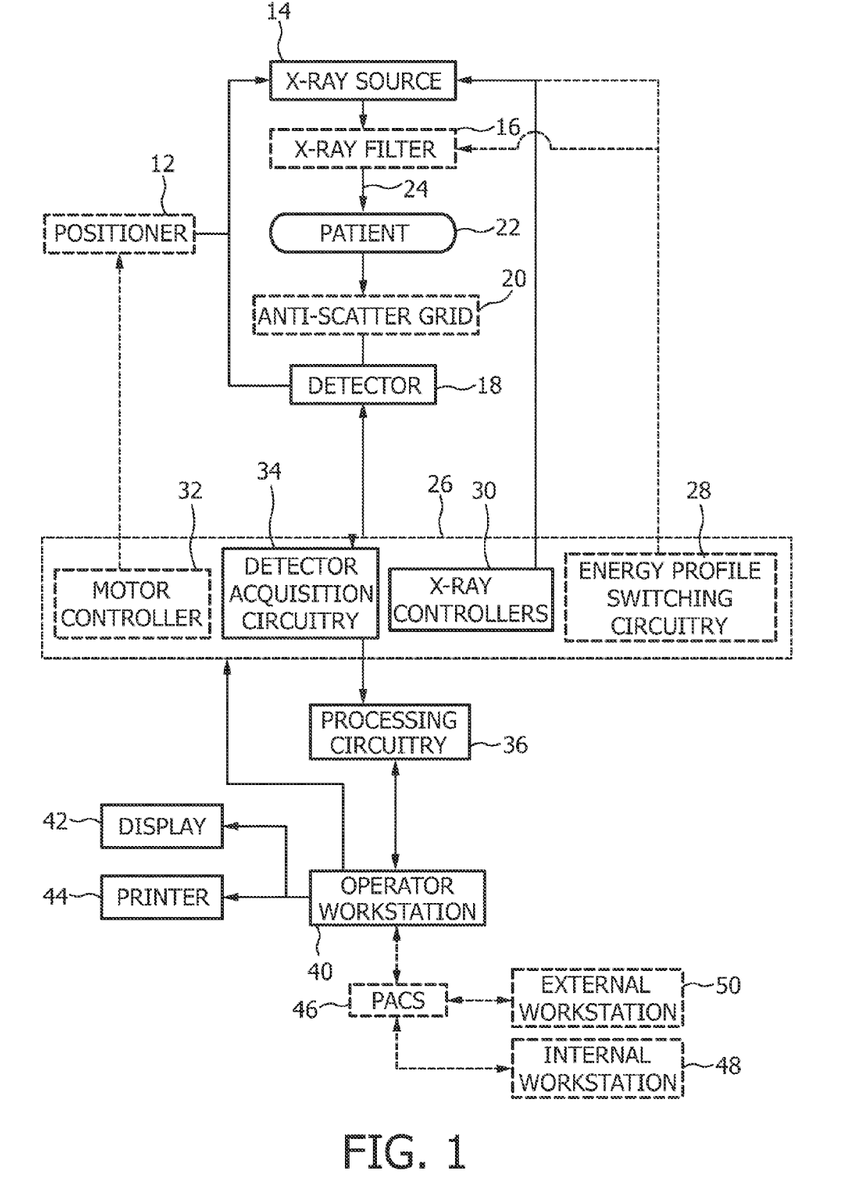
FIG. 1 shows schematically an embodiment of an examination apparatus according to the present invention.

FIG. 1 shows a schematic view of an exemplary embodiment of a multi-energy examination apparatus 10 in accordance with the present invention. The apparatus 10 includes a positioner or a support 12 that supports an X-ray source unit 14. The support 12 may include one or more X-ray filters 16 which may be positioned between the X-ray source unit 14 and the imaging volume as desired. A digital detector 18, such as a flat panel detector, is generally situated across the imaging volume from the X-ray source unit 14 and may be stationary or may move in coordination with or independent from the X-ray source unit 14 and/or support 12. An anti-scatter grid 20 may also be present between the digital detector 18 and the imaging volume. When present, the anti-scatter grid 20 is typically mounted close to the digital detector 18 to reduce the incidence of scattered X-ray on the digital detector 18. In one embodiment, the anti-scatter grid may be steerable. In another embodiment, no anti-scatter grid may be present but algorithmic scatter correction may instead be performed to obtain quantitative projection images.

The X-ray source unit 14 is configured to emit X-rays from multiple locations, within a limited angular range, toward all or part of a patient 22 situated within an imaging volume that encompasses a region of interest in the patient 22. The X-ray source unit 14 may be movable in one, two or three dimensions to different locations, either manually or by automated means, such that the X-ray source unit 14 may change position relative to the patient 22, and/or the digital detector 18.

Figure 2:
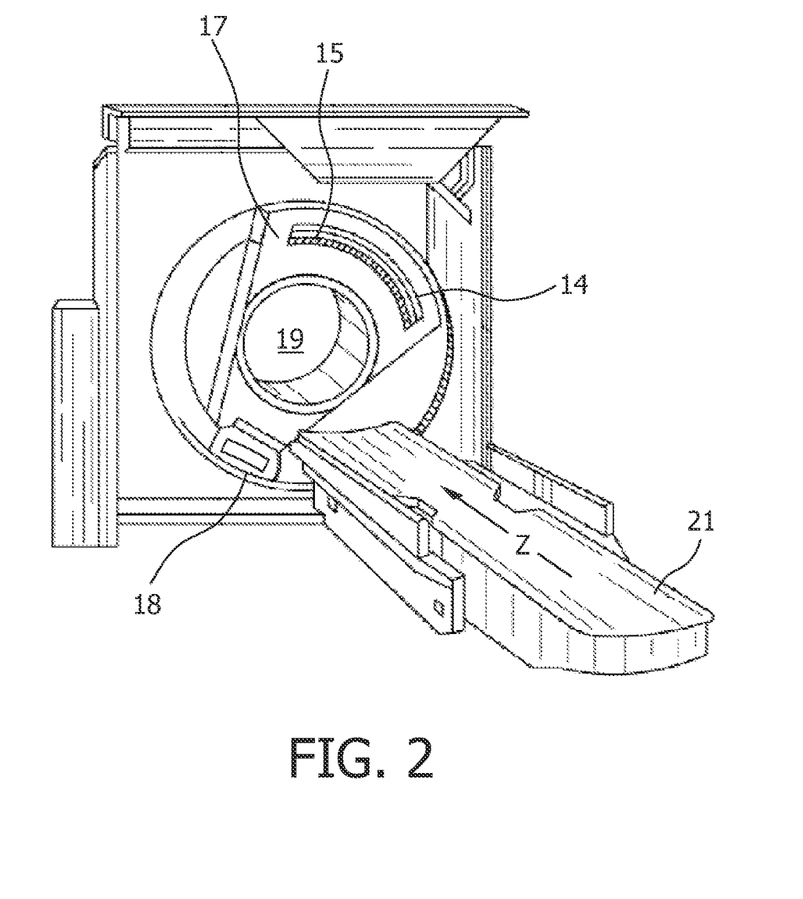
FIG. 2 shows an implementation of said embodiment shown in FIG. 1 in a CT arrangement.

Preferably, in a CT arrangement, as shown in FIG. 2, the X-ray source unit 14 (comprising a number of distributed X-ray sources 15) and the X-ray detector 18 are mounted on a gantry 17 so as to rotate around the examination area 19. A support 21 such as a table supports a patient or other object in the examination area 19. The patient support 21 is preferably movable in the longitudinal or z-direction. However, in a different embodiment, the X-ray source unit 14 and the X-ray detector 18 are stationary and not mounted on a gantry.

Typically, the X-ray source unit 14 is configured to emit X-rays at one or more spectra useful for imaging the desired object or patient 22. For example, in a medical context, the X-ray source may emit a spectrum of X-ray radiation with high-energy photons, e.g. a copper-filtered 140 kVp spectrum, which may be used for patient imaging or may emit X-rays at one or more low-energy spectra (e.g. unfiltered 90 kVp spectrum) which are each useful for patient imaging based on the desired transmission characteristics of the X-rays. X-rays may be emitted from the X-ray source unit 14 at a number of locations by a number of generators located at or moved to desired emission locations of the X-ray radiation. (i.e., an X-ray tube situated at each desired emission location) or a mixture of stationary and mobile X-ray tubes 15 located at or capable of moving to the desired emission locations within the desired angular range.

The X-ray source 14, as described above, emits X-ray radiation 24 (see FIG. 1) through the patient 22 towards the digital detector 18. The digital detector 18 typically includes an array of detector elements configured to generate digital signals in response to the X-ray radiation 24. In one embodiment of the present invention, the digital detector 18 does not discriminate between the energies of the different photons impacting a pixel, i.e., each pixel accumulates and represents the charge information for a variety of X-ray spectra. In such an embodiment, an X-ray filter 16 may be used to allow differentiation of X-ray energies by limiting or modifying the transmitted spectra at different times, such as for alternating X-ray emissions. The X-ray filter 16 may be made of copper, aluminum, iron, molybdenum, tin, barium, gadolinium, tungsten, lead or other suitable material. Alternatively, in another embodiment of the present invention, the X-ray source 14 may be configurable to emit X-rays at two or more spectra such that X-rays having offset spectra or energy profiles may be transmitted at different times without the use of a filter 16.

Alternatively, in yet another embodiment, the X-ray source unit 14 is not filtered or configured (or only partly filtered or at special positions only) to emit at two or more spectra, however the digital detector 18 may be an energy discriminating detector, which by itself is capable of distinguishing the X-ray radiation 24 having different energy profiles or levels. For example, in one embodiment, the energy discriminating detector is used to capture both high-energy and low-energy images for a particular position of the X-ray source in one exposure. Similarly, in another embodiment, the digital detector 18 may include stacked arrays of scintillators and photodiodes in which each stack is configured to detect X-rays having different spectra or energy profiles. In this embodiment, the digital detector 18 may be used to capture high and low-energy images simultaneously.

The operation of the X-ray source unit 14 may be controlled by a system controller 26. For example, the system controller 26 controls the activation and operation, including collimation and timing, of the X-ray source unit 14 via X-ray controller 30. Furthermore, in embodiments in which the X-ray source unit 14 is configured to emit X-rays at more than one energy profile, the system controller 26 may be configured to control or select the energy profile of an X-ray emission via an energy profile switching circuitry 28.

The motion of the X-ray source unit 14 and/or the digital detector 18 may also be controlled by the system controller 26, such as by the motor controller 32, to move independently of one another or to move in synchrony. For example, in one embodiment, the motor controller 32 may control the operation of the positioner 12, such as a C-arm, to which the X-ray source unit 14 and/or digital detector 18 are physically attached. In general, the positioner 12 provides the physical motion of the X-ray source unit 14 and/or the digital detector 18 in accordance with a pre-defined or operator selected imaging trajectory. Hence by means of the positioner 12, the system controller 26 may facilitate the acquisition of radiographic projections at various angles through the patient. Alternatively, in embodiments in which the X-ray source unit 14 and digital detector 18 are stationary, that is, where the X-ray source unit 14 comprises multiple X-ray tubes or solid state-emitters fixed at different angles relative to the detector 18, no positioner 12 is present. Alternative and hybrid configurations are possible as well, for example, in one embodiment, multiple X-ray sources may be employed which move as a set (i.e., not individually). In addition, in some embodiments, the patient or the object being imaged may be moved relative to the X-ray source(s) and/or detector to generate the projection angles at different views over the limited angular range.

The system controller 26 may also control the operation and readout of the digital detector 18, such as through detector acquisition circuitry 34. In one embodiment, the digital detector 18 converts analog signals acquired in response to the X-ray radiation to digital signals and provides the same to detector acquisition circuitry 34 for further processing. Processing circuitry 36 is typically present to process and reconstruct the data read out from the digital detector 18 by the detector acquisition circuitry 34. In particular, projection data or projection images are typically generated by the detector acquisition circuitry 34 in response to the X-rays emitted by the X-ray source unit 14. In embodiments in which the X-rays are generated or filtered to have different spectra or energy profiles at different times, the projection images may be acquired at a particular energy profile in all defined locations and the process may be repeated for other energy profiles. Alternatively, the projection images may also be acquired for all of the energy profiles at a particular location and the process may be repeated for all defined locations. Other acquisition sequences are possible as well. However, in embodiments employing an energy discriminating detector as the digital detector 18, only one projection image is typically acquired at each location as each projection image includes the desired energy information. The projection data collected by the detector 18 may undergo pre-processing at the detector acquisition circuitry 34 and/or the processing circuitry 36. In addition, the processing circuitry 36 may reconstruct the projection data to generate one or more three-dimensional images for display.

The processing circuitry 36 may decompose the projection images based on energy characteristics such that different energy characteristics are associated with different material types. The processing circuitry 36 may further reconstruct the projection images to generate three-dimensional images, such as tomosynthesis images. The steps of reconstruction and decomposition may be performed in either order, but, in general, when both steps are performed, composition three-dimensional tomosynthesis images, which represent different material or tissue types, can be generated. For example, composition tomosynthesis images may include a soft tissue tomosynthesis image, a bone-tomosynthesis image, and/or a contrast image. Conversely, if the processing circuitry reconstructs the acquired projection data without also decomposing the projection data, energy tomosynthesis images, such as a low-energy tomosynthesis image, an intermediate-energy image and a high-energy tomosynthesis image may be generated. These energy tomosynthesis images depict the attenuation of X-rays at the respective energy profile by the patient 22 or object in the imaging volume. In a medical context, the various tomosynthesis images reveal an internal region of interest of the patient 22, which may be used for further diagnosis. The processing circuitry 36 may also include memory circuitry to store the processed and to be processed data. The memory circuitry may also store processing parameters, and/or computer programs.

The processing circuitry 36 may be connected to an operator workstation 40. The images generated by the processing circuitry 36 may be sent to the operator workstation 40 for display, such as on the display 42. The processing circuitry 36 may be configured to receive commands or processing parameters related to the processing or images or image data from the operator workstation 40, which may include input devices such as a keyboard, a mouse, and other user interaction devices (not shown). The operator workstation 40 may also be connected to the system controller 26 to allow an operator to provide commands and scanning parameters related to the operation of the X-ray source unit 14 and/or the detector 18 to the system controller 26. Hence an operator may control the operation of all or part of the system 10 via the operator workstation 40.

The operator workstation 40 is typically connected to a display 42 and/or to a printer 44 capable of rendering the images generated by the processing circuitry 36. Display and/or printer circuitry within the operator workstation 40 typically provides the images to the respective display 42 or printer 44 for rendering. Further the operator workstation 40 may also be connected to a picture archiving system (PACS) 46, which may in turn be connected to an internal workstation 48 and/or an external workstation 50 through networks so that people at different locations may gain access to the images and/or image data. Similarly, the operator workstation 40 may access images or data accessible via the PACS 46 for processing by the processing circuitry 36 and/or rendition on the display 42 or printer 44.

Figure 3:
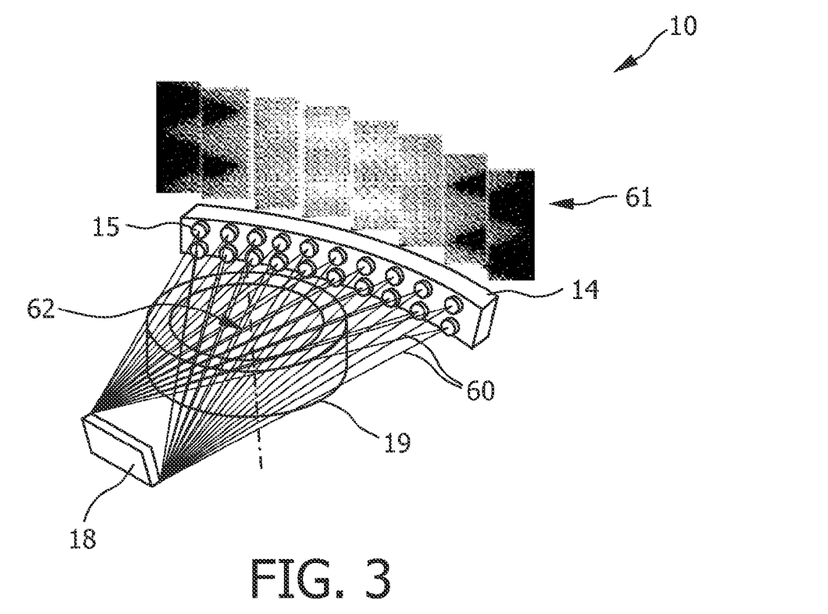
FIG. 3 shows a three-dimensional perspective view of a multi-source IGCT system.

FIG. 3 shows a three-dimensional perspective view of a multi-source Inverse Geometry Computed Tomography (IGCT) system 10, which uses a small detector 18 combined with a large distributed source unit 14, on which multiple x-ray point sources 15 are arrayed trans-axially (in the xy-plane) and longitudinally (along the z-axis). Each x-ray point source 15 emits a fan-beam (or a cone-beam) 60 at different times, and the projection data (e.g., sinograms) 61 is captured by the detector 18. Additionally, the detector 18, the distributed source unit 14, and the fan beams (or cone-beams) 60 may be axially rotated about a rotational axis 62. The projection data 61 captured by the detector 18 is processed to reconstruct an object of interest within the field of view (examination area) 19. A known re-binning algorithm may be used to re-bin the projection data into parallel ray projections.

Trans-axially, the multiple x-ray point sources 15 are positioned preferably on an iso-centered arc so that all corresponding fan beams (or cone beams) 60 can be rotated to fit into conventional third generation system with an iso-focused detector. This makes exact re-binning to full cone beams possible and also helps to achieve a uniform beam profile. The resulting dataset can be re-arranged or re-binned into multiple longitudinally offset third-generation datasets. An algorithm developed for multiple x-ray point sources 15 distributed in z can also be applied to multiple longitudinally-offset axial scans with a conventional third generation CT, and vice versa. While positioning the sources on isocentric arcs is desirable for these reasons, other arrangements, such as detector-centered arcs and flat arrays, can also be used.

While X-ray tubes are one possibility for X-ray generation by the X-ray source unit 14, in other embodiments the X-ray source unit 14 may employ other X-ray generation and emission techniques. For example, the X-ray source unit 14 may employ a solid-state X-ray emitters in place of the X-ray tubes in the implementations described above. However, while X-ray tubes and solid-state X-ray emitters are two examples of X-ray generation and emission techniques which may be employed, other X-ray generation techniques or devices capable of generating X-rays having medically (or industrially) useful spectra may also be employed in conjunction with the present techniques.

Figure 4:
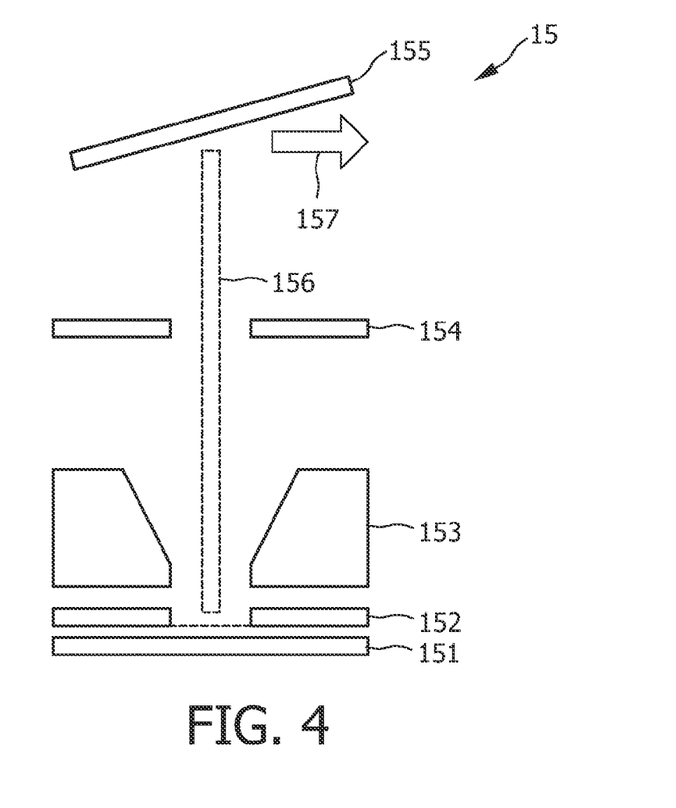
FIG. 4 shows an embodiment of a carbon nanotube based field emission X-ray source.

In an embodiment, for instance, an array of carbon nanotube (CNT) based field emission X-ray sources 15 is used for X-ray generation. Each source 15 of the array 14 comprises, as shown in FIG. 4, a CNT cathode 151, a gate electrode 152, one or two focusing electrodes 153, 154 and an anode 155 where conversion of the electron beam 156 to X-rays 157 takes place. On- and off-switching of individual sources is preferably accomplished by applying appropriate voltages to the gate electrode 152.

According to the present invention the system controller 26, in particular energy profile switching circuitry 28 and/or the X-ray controller 30, is adapted for controlling said X-ray sources 15 to separately and subsequently emit X-rays at least two different energy spectra such that in the time interval, during which a particular X-ray source is switched over to emit X-rays at a different energy spectrum, said particular X-ray source is switched off and one or more other X-ray sources are separately and subsequently switched on to emit X-rays. Thus, according to the present invention an alternating kV modulation scheme is applied.

Figure 5:
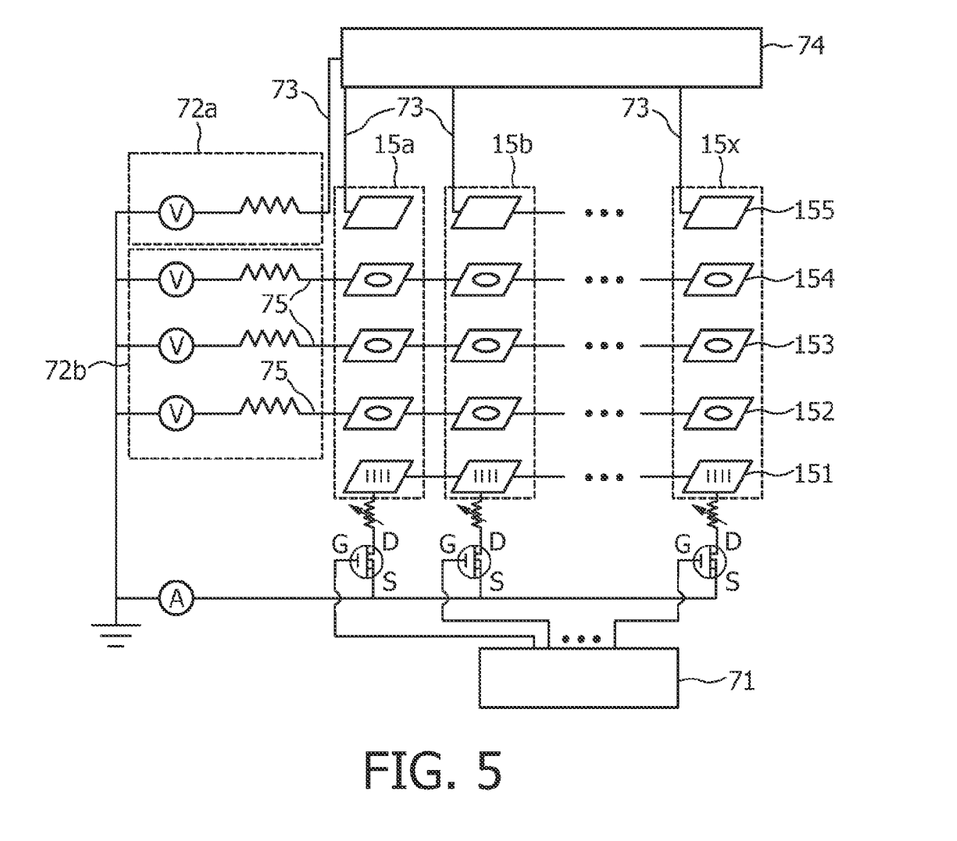
FIG. 5 shows an embodiment of an energy profile switching circuitry.

An appropriate implementation of an energy profile switching circuitry 28 for individually controlling and switching a number of x-ray sources 15a, 15b, . . . , 15x is shown in FIG. 5.

Figure 6:
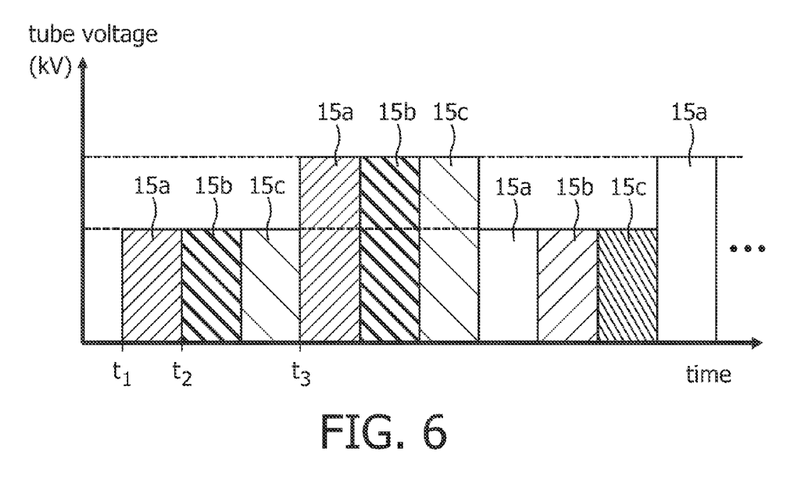
FIG. 6 shows a diagram illustrating a switching scheme for the X-ray sources according to the present invention.

FIG. 6 shows a diagram illustrating a switching scheme for the X-ray sources according to the present invention. For instance, regard a particular source 15a which is switched on at time $t_1$ with a high-voltage $U_1$ and switched off at time $t_2$. After that scanning proceeds with other sources 15b, 15c of the X-ray generator. At time $t_3$ source 15a is activated again with high-voltage $U_2$. During the time interval between $t_2$ and $t_3$ the high voltage source for source 15a is switched from $U_1$ to $U_2$. Changing the high voltage takes some time which is usually given by the RC time constant of the high voltage supply lines.

Thus, the described technique benefits from the fast switching of tubes (e.g. CNTs) in the current domain, thereby relaxing the hardware effort for the high-voltage switching unit. In particular, the anode of the sources 15a, 15b, 15c can be coupled during the time interval from $t_1$ to $t_2$ to voltage $U_1$. At time $t_2$ the anode of the source 15a can already be switched to voltage $U_2$, is however only activated at time $t_3$ by use of the gate voltage. This activation is achieved with high speed, if CNTs are used as sources, while the switching of the high voltage from $U_1$ to $U_2$ by use of a high voltage switch can be done more slowly. By this decoupling of the high voltage switching of the anode voltage from the activation via the gate voltage the described advantage of the use of switching sequences is achieved.

Preferably, the examination apparatus, in particular the inverse CT system, proposed according to the present invention is equipped with a multi-layer detector. The advantage compared to a multi-layer detector and conventional CT geometry is that the hardware costs are reduced, because detectors in inverse geometry cover a smaller X-ray sensitive area. Thus, in an embodiment a source switching pattern with two high-voltage settings, as shown in FIG. 6, and a dual-layer detector forms the inverse-geometry implementation of "Quad-Energy CT".

In an alternative embodiment, the examination apparatus, in particular the inverse CT system, proposed according to the present invention is equipped with an energy-discriminating counting-mode detector. Again, the advantage is a reduction of hardware costs due to less detector area. Counting-mode detectors cover a limited dynamic range of X-ray intensities. In order to better cope with this feature, a control loop, which contains detector pixels and X-ray sources, for regulating X-ray intensity can be set up. In this way the imaging system has a detector with active dose sensing capability in conjunction with an X-ray source which has a virtual bow-tie filter. One implementation of the control loop, e.g., performs a reduction the X-ray source current if there is an indication that at least one of the detector pixels saturates in count rate.

In preferred embodiments there is a multitude of high voltage lines 73, as shown in FIG. 5, of typically up to 150 kV which are supplied by a high-voltage generator unit 72a comprising one or more high-voltage generators. There can be, for instance, two high-voltage generators for dual energy supply or three high-voltage generators for triple energy supply with fixed voltages. Alternatively, there can be two high-voltage generators, wherein one of the generators provides a voltage to the active X-ray source(s) and the other generator is switched to the next (higher or lower) voltage, needed next.

This can be realized by using the lowest high voltage setting as reference and adding a certain amount of electrical potential for the other settings. The anodes 155 of individual sources 15a, 15b, . . . , 15x are dynamically connected to distinct high voltage lines 73. The corresponding focusing electrodes 153, 154 and the gate electrode 152 of each source are connected to additional voltage supplies 72b and are set to fixed fractions of the anode potential. A time-controlled multiplexer 74 dynamically connects sets of anodes 154 (and, according to alternative embodiments, focusing electrodes 153, 154 and gate electrodes 152) to respective high voltage supply lines 73 (for the anodes), 75 (for the focusing electrodes 153, 154 and the gate electrodes 152) according to the source switching pattern. The multiplexer 74 is, for instance, controlled by a microprocessor or FPGA 71 which is also connected to the data acquisition system (34 in FIG. 1) for time synchronization of X-ray generator and detector.

In an embodiment, a pixelated detector with a top layer of gadoliniumoxisulfide (GOS) and a bottom layer of GOS with photodiode readout at the side is used.

Figure 7:
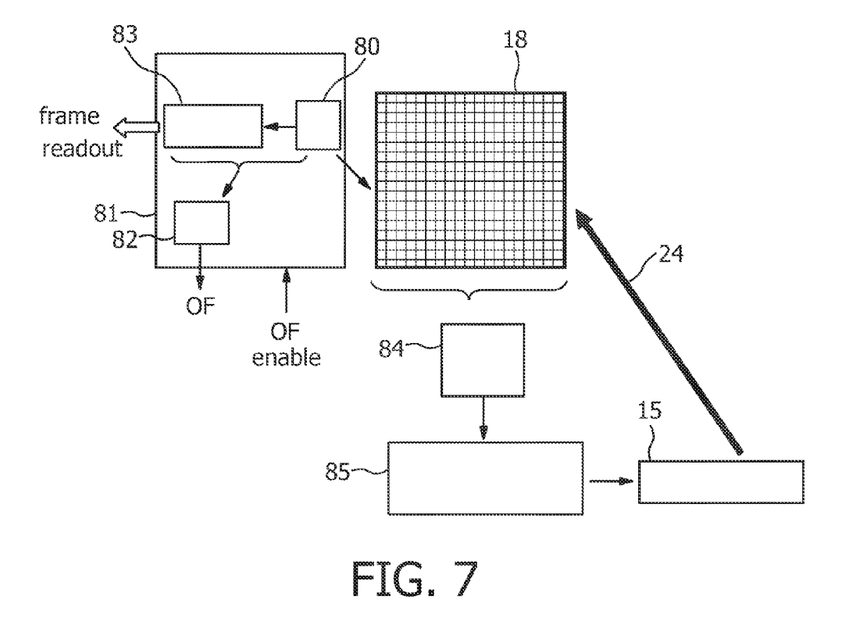
FIG. 7 shows a block diagram of an embodiment of a control loop for an examination apparatus according to the present invention.

According to another embodiment a pixelated semiconductor sensor, e.g. made of Cd(Zn)Te, and associated counting electronics which, e.g., has a shaping amplifier, discriminators and corresponding counters in each pixel, are used. A block diagram of an embodiment of a control loop for such an embodiment of the examination apparatus is shown in FIG. 7. Said control loop prevents count-rate saturation in the detector pixels of the detector 18. In each electronic pixel 80 there is an overflow detection unit 81 which outputs overflow flags (OF) 82. Overflow detection is performed within in a predefined time interval ('sub-frame') which is shorter than the frame time for readout of counter 83. The sub-frame time interval is defined by the digital signal OF enable. After each sub-frame the OFs of all pixels are combined by an OR circuitry 84 which can be performed rather fast. If at least one pixel indicated overflow, tube current is reduced by a current control unit 85, and counters 83 of saturated pixels are reset. The loop comprising overflow detection and current reduction stops if no pixel indicates overflow. Frame readout of the counters 83 preferably also captures the number of resets in a channel during an acquisition time frame. In that way no photon registrations are lost for pixels which do not suffer from overflow and pixels with overflow in the sub-frame(s) still have reasonable statistics. The OF can be derived from entries in the counter 83, time-over-threshold information, or from integrated-charge in the sub-frame, which is, e.g., measured with CIX-type readout electronics (simultaneous counting and integrating facilitated by appropriate electronics based on signal duplication).

The geometry of examination apparatus is chosen according to the application. As mentioned above, in one scenario source array and detector are mounted on a CT gantry and rotate around the object during data acquisition. In another scenario detector and source array remain stationary and the object is sampled at a reduced set of view angles.

Image reconstruction is done according to various techniques. One applicable technique is tomosynthesis as described, e.g. in Dobbins J., "Digital x-ray tomosynthesis: current state of the art and clinical potential", Phys. Med. Biol. 48 (2003) R65-R106. However, other techniques can be applied as well, such as filtered backprojections (Feldkamp) or iterative algorithms, which are per se well known in the art. In this mode the frame time can be dynamically adapted according to the final beam intensity set by the control loop.

It is also possible that a single anode serves as a common anode for a couple of emitters, or that there are a couple of anodes provided for a single emitter. For instance, anodes of different materials can be provided, e.g. to emit different or overlapping energy spectra.

Figure 8:
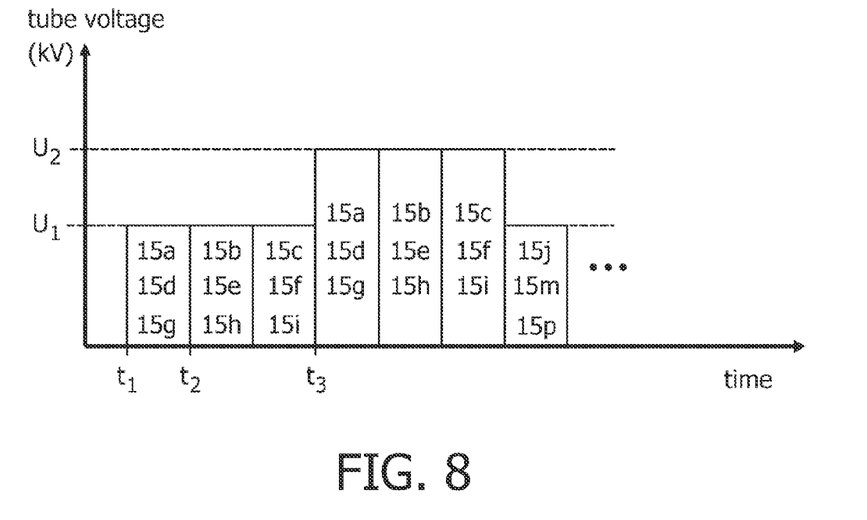
FIG. 8 shows a diagram illustrating another switching scheme for the X-ray sources according to the present invention.

FIG. 8 shows a diagram illustrating another switching scheme for the X-ray sources according to the present invention. According to this embodiment the X-ray sources are not switched on one at a time but are switched on in groups. For instance, a first group of sources 15$a$, 15$d$, 15$g$ is switched on at time $t_1$ with a high-voltage $U_1$ and switched off at time $t_2$. After that scanning proceeds with another group of sources 15$b$, 15$e$, 15$h$ and thereafter with the group of sources 15$c$, 15$f$, 15$i$ of the X-ray generator. At time $t_3$ the first group of sources 15$a$, 15$d$, 15$g$ is activated again with high-voltage $U_2$. During the time interval between $t_2$ and $t_3$ the high voltage source for the group of sources 15$a$, 15$d$, 15$g$ is switched from $U_1$ to $U_2$.

Preferably, the X-ray sources assigned to a particular group have no or little overlap in the energy spectra. An energy-resolving detector is used which is tuned such that registered photons can be assigned to one of the active sources with high probability. In this way the Poisson error is quite low in contrast to the conventional approach where two (large) numbers with a high resulting quantum noise would have to be subtracted. An advantage is again fast timing with less motion artefacts.

The main application of the invention is Computed Tomography with energy resolution, or projection imaging with energy resolution or any other application that may benefit from energy-resolving X-ray photon counting.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An X-ray examination apparatus comprising:
an X-ray source unit comprising a plurality of X-ray sources for emitting X-rays at a plurality of locations,
an X-ray detection unit for detecting X-rays emitted from one or more of said X-ray sources after penetration of an examination area between said X-ray source unit and said X-ray detection unit and for generating detection signals,
a processing unit for processing the generated detection signals, and
a control unit for controlling said X-ray sources to subsequently, alone or in groups emit X-rays at at least two different energy spectra such that in the time interval, during which a particular X-ray source or said group of X-ray sources is switched over to emit X-rays at a different energy spectrum, said particular X-ray source or said group of X-ray sources is switched off and one or more other X-ray sources or groups of X-ray sources are subsequently switched on to emit X-rays, wherein said control unit dynamically connects said X-ray sources to high voltage supply lines of the high voltage supply unit according to a switching pattern.

2. The X-ray examination apparatus as claimed in claim 1, wherein said control unit is adapted for controlling said X-ray sources such that the particular X-ray source or said group of X-ray sources is switched over to emit X-rays at said different energy spectrum.

3. The X-ray examination apparatus as claimed in claim 1, wherein said control unit is adapted for controlling said X-ray sources such that said one or more other X-ray sources or said group of X-ray sources, which are subsequently switched on to emit X-rays during said time interval during which said particular X-ray source or said group of X-ray sources is switched over, are emitting X-rays at the energy spectrum, at which said particular X-ray source or said group of X-ray sources had previously emitted X-rays or will emit X-rays after it has been switched over.

4. The X-ray examination apparatus as claimed in claim 1, wherein said control unit is adapted for controlling said X-ray sources to emit X-rays in groups such that X-ray sources of a first group of X-ray sources are alone, separately and subsequently emitting X-rays at the at least two different energy spectra and that thereafter X-ray sources of other groups of X-ray sources are alone, separately and subsequently emitting X-rays at the at least two different energy spectra.

5. The X-ray examination apparatus as claimed in claim 1, wherein said control unit is adapted for switching over said X-ray sources to emit X-rays at a different energy spectrum by changing the voltage provided to the anode of an X-ray source.

6. The X-ray examination apparatus as claimed in claim 5, wherein said control unit comprises a multiplexer that dynamically connects said X-ray sources to the high voltage supply lines.

7. The X-ray examination apparatus as claimed in claim 1, wherein said X-ray sources are microfocus X-ray sources with carbon nanotube based field emitter.

8. The X-ray examination apparatus as claimed in claim 1, further comprising a gantry on which said X-ray source unit and said X-ray detection unit are mounted and which is configured to rotate around said examination area.

9. The X-ray examination apparatus as claimed in claim 1, wherein said X-ray detection unit comprises a multi-layer detector, in particular a dual-layer detector, each layer being adapted for detecting X-rays at a predetermined energy spectrum.

10. The X-ray examination apparatus as claimed in claim 1, wherein said X-ray detection unit comprises a energy discriminating, photon counting detector.

11. The X-ray examination apparatus as claimed in claim 10, further comprising overflow detection means for detecting if during an X-ray detection there is an overflow in any pixel of the X-ray detector, and
wherein said control unit is adapted to reduce the current provided to the active X-ray source.

12. The X-ray examination apparatus as claimed in claim 1, wherein said control unit is adapted for controlling said X-ray sources to emit X-rays in groups such that a first group of X-ray sources are emitting X-rays with overlapping energy spectra and that thereafter other groups of X-ray sources are separately and subsequently emitting X-rays at, in particular the same, energy spectrum.

13. An X-ray examination method comprising:
emitting X- at a plurality of locations by an X-ray source unit comprising a plurality of X-ray sources,
detecting X-rays emitted from one or more of said X-ray sources after penetration of an examination area between said X-ray source unit and an X-ray detection unit and generating detection signals,
processing the generated detection signals,
detecting if during an X-ray detection there is an overflow in any pixel of the X-ray detection unit; and
controlling said X-ray sources to subsequently, alone or in groups emit X-rays at at least two different energy spectra such that in the time interval, during which a particular X-ray source or said group of X-ray sources, is switched over to emit X-rays at a different energy spectrum, said particular X-ray source or said group of X-ray sources is switched off and one or more other X-ray sources or groups of X-ray sources are separately and subsequently switched on to emit X-rays, wherein the controlling further comprises reducing the current provided to the active X-ray source if the overflow in any pixel is detected.

14. Computer program comprising program code means for causing a computer to control the X-ray examination apparatus as claimed in claim 1 when said computer program is carried out on a computer.

15. The system of claim 1, wherein the X-ray detection unit includes stacked arrays of scintillators and photodiodes in which each stack is configured to detect X-rays having different energy profiles.

16. The system of claim 1, wherein the X-ray source unit comprises field emitter based X-ray sources.

17. The system of claim 6, wherein the multiplexer is controlled by a microprocessor and connected to a data acquisition system for time synchronization of the X-ray source unit and the X-ray detection unit.

18. The method of claim 13, further comprising dynamically connecting said X-ray sources to supply lines of the high voltage supply unit according to a switching pattern.

19. The method of claim 13, wherein overflow detection is performed within a predefined time interval that is shorter than a time period of the readout of a counter.

20. An X-ray examination apparatus comprising:
means for emitting X-rays at a plurality of locations,
means for detecting X-rays emitted after penetration of an examination area between said means for emitting and said means for detecting, wherein the means for detecting further generates detection signals,
means for processing the generated detection signals, and
means for controlling said X-ray sources to subsequently, alone or in groups emit X-rays at at least two different energy spectra by changing the voltage provided to the anode of the means for emitting such that in the time interval, during which the means for emitting is switched over to emit X-rays at a different energy spectrum, wherein the means for emitting is switched off and the means for emitting is subsequently switched on to emit X-rays, wherein said means for controlling dynamically connects said means for emitting to high voltage supply lines of a means for supplying high voltage according to a switching pattern.

* * * * *